United States Patent
Huang et al.

(10) Patent No.: US 10,008,971 B2
(45) Date of Patent: Jun. 26, 2018

(54) MONITOR CIRCUIT AND MONITORING METHOD

(71) Applicant: Delta Electronics, Inc., Taoyuan (TW)

(72) Inventors: Yueh-Lung Huang, Taoyuan (TW); Jung-Yuan Chen, Taoyuan (TW); Ching-Sen Hsieh, Taoyuan (TW); Yu-Cheng Lin, Taoyuan (TW); Nai-Wen Hsu, Taoyuan (TW)

(73) Assignee: Delta Electronics, Inc., Taoyuan (TW)

( * ) Notice: Subject to any disclaimer, the term of this patent is extended or adjusted under 35 U.S.C. 154(b) by 0 days. days.

(21) Appl. No.: 15/198,209

(22) Filed: Jun. 30, 2016

(65) Prior Publication Data

US 2017/0276512 A1 Sep. 28, 2017

(30) Foreign Application Priority Data

Mar. 25, 2016 (CN) .......................... 2016 1 0180311

(51) Int. Cl.
| | |
|---|---|
| *G01R 31/02* | (2006.01) |
| *H02P 1/00* | (2006.01) |
| *H02P 29/00* | (2016.01) |
| *G01N 21/94* | (2006.01) |
| *G06F 1/20* | (2006.01) |
| *G01D 5/14* | (2006.01) |
| *G01N 21/85* | (2006.01) |

(52) U.S. Cl.
CPC ......... *H02P 29/0044* (2013.01); *G01N 21/94* (2013.01); *G01D 5/145* (2013.01); *G01N 21/85* (2013.01); *G06F 1/20* (2013.01)

(58) Field of Classification Search
None
See application file for complete search history.

(56) References Cited

U.S. PATENT DOCUMENTS

| | | | | |
|---|---|---|---|---|
| 7,234,818 B2* | 6/2007 | Hsieh | ...................... | G03B 21/26 250/222.2 |
| 7,792,597 B2* | 9/2010 | Brey | ...................... | G06F 1/206 700/299 |
| 7,808,192 B2* | 10/2010 | Ma | ............................ | G06F 1/20 318/268 |
| 2007/0008109 A1* | 1/2007 | Wang | ..................... | G08B 21/10 340/539.11 |
| 2007/0133955 A1* | 6/2007 | Hsu | ....................... | F04D 27/004 388/811 |
| 2010/0181950 A1* | 7/2010 | Tu | ............................ | H02P 1/30 318/400.11 |
| 2013/0156576 A1* | 6/2013 | Warren | .............. | H05K 7/20172 416/1 |

* cited by examiner

*Primary Examiner* — Bentsu Ro
*Assistant Examiner* — Zemenay Truneh
(74) *Attorney, Agent, or Firm* — Muncy, Geissler, Olds & Lowe, P.C.

(57) ABSTRACT

The invention provides a monitor circuit, which is used for a fan and receives a driving current and a driving voltage of the fan. The monitor circuit includes sensing circuits and a microcontroller. The sensing circuits respectively sense statuses of the fan and output sensing values. The microcontroller is used for monitoring whether the sensing values exceed preset value ranges respectively to obtain comparison results. The microcontroller outputs warning signals according to the comparison results. Each of the warning signals has a specific frequency.

20 Claims, 8 Drawing Sheets

| condition | specific frequency (Hz) | S1 | S2 | S3 | S4 | S5 |
|---|---|---|---|---|---|---|
| 1 | 10 | 1 | 0 | 0 | 0 | 0 |
| 2 | 20 | 0 | 1 | 0 | 0 | 0 |
| 3 | 30 | 0 | 0 | 1 | 0 | 0 |
| 4 | 40 | 0 | 0 | 0 | 1 | 0 |
| 5 | 50 | 0 | 0 | 0 | 0 | 1 |
| 6 | 60 | 1 | 1 | 0 | 0 | 0 |
| 7 | 70 | 1 | 0 | 1 | 0 | 0 |
| 8 | 80 | 1 | 0 | 0 | 1 | 0 |
| 9 | 90 | 1 | 0 | 0 | 0 | 1 |
| 10 | 100 | 0 | 1 | 1 | 0 | 0 |
| 11 | 110 | 0 | 1 | 0 | 1 | 0 |
| 12 | 120 | 0 | 1 | 0 | 0 | 1 |
| 13 | 130 | 0 | 0 | 1 | 1 | 0 |
| 14 | 140 | 0 | 0 | 1 | 0 | 1 |
| 15 | 150 | 0 | 0 | 0 | 1 | 1 |
| 16 | 160 | 1 | 1 | 1 | 0 | 0 |
| 17 | 170 | 1 | 0 | 1 | 1 | 0 |
| 18 | 180 | 1 | 0 | 0 | 1 | 1 |
| 19 | 190 | 0 | 1 | 1 | 1 | 0 |
| 20 | 200 | 0 | 1 | 0 | 1 | 1 |
| 21 | 210 | 1 | 1 | 0 | 0 | 1 |
| 22 | 220 | 0 | 0 | 1 | 1 | 1 |
| 23 | 230 | 1 | 0 | 1 | 0 | 1 |
| 24 | 240 | 1 | 1 | 1 | 1 | 0 |
| 25 | 250 | 0 | 1 | 1 | 1 | 1 |
| 26 | 260 | 1 | 0 | 1 | 1 | 1 |
| 27 | 270 | 1 | 1 | 1 | 1 | 1 |

FIG. 7

MONITOR CIRCUIT AND MONITORING METHOD

CROSS REFERENCE TO RELATED APPLICATIONS

This Application claims priority of China Patent Application No. 201610180311.X, filed on Mar. 25, 2016, the entirety of which is incorporated by reference herein.

BACKGROUND OF THE INVENTION

Field of the Invention

The present invention relates to a monitor circuit and a monitoring method and in particular to a monitor circuit and a monitoring method for monitoring statuses of a fan.

Description of the Related Art

With the progress currently being made in several fields of technology, various electronic devices, such as computers, servers, etc., have become indispensable parts of modern-daily life. The capability of these electronic devices to dissipate heat always affects their stability while in operation, as well as the overall service life. Therefore, in order to enhance the efficiency of heat dissipation, an additional fan may be disposed inside the electronic device or in an environment where the electronic device is placed, so as to decrease the temperature of the electronic device.

However, the fan circuits presently in use can only notify the user when a problem occurs with the fan, but they cannot provide further details, such as problems with rotation speed, driving voltage, driving current, or temperature. Consequently, it is important to develop a circuit which can monitor various statuses of the fan.

BRIEF SUMMARY OF THE INVENTION

For the reasons listed above, the present invention provides a monitor circuit for monitoring various statuses of a fan, so as to solve problems.

The invention provides an embodiment of a monitor circuit. The monitor circuit is used in a fan and receives the driving current and driving voltage of the fan. The monitor circuit includes a plurality of sensing circuits and a microcontroller. The sensing circuits respectively sense a plurality of statuses of the fan and output a plurality of sensing values. The microcontroller is used for monitoring whether the sensing values exceed a plurality of preset value ranges respectively to obtain a plurality of comparison results. The microcontroller outputs one of a plurality of warning signals according to the comparison results. Each of the warning signals has a specific frequency.

The invention further provides a monitoring method including: sensing a plurality of statuses of a fan by a plurality of sensing circuits respectively to obtain a plurality of sensing values; monitoring whether the sensing values exceed a plurality of preset value ranges respectively to obtain a plurality of comparison results; and outputting one of a plurality of warning signals by the microcontroller according to the comparison results; wherein each of the warning signals comprises a specific frequency.

The invention provides a monitor circuit for monitoring various statuses of a fan. The monitor circuit can monitor whether a total number of rotations of the fan exceeds a preset rotation number, monitor whether the driving voltage and the driving current are within the respective ranges of a rated voltage and a rated current, and monitor whether the temperature of the fan exceeds a preset temperature, etc.

Therefore, the invention can solve the problems in the prior art with conventional fans only being able to detect problems with the fan, but not being able to provide any further detailed information about the fan to generate a specific warning signal.

BRIEF DESCRIPTION OF THE DRAWINGS

The present invention can be more fully understood by reading the subsequent detailed description and examples with references made to the accompanying drawings, wherein:

FIG. 7 is a diagram of a comparison table stored in a microcontroller according to an embodiment of the invention.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
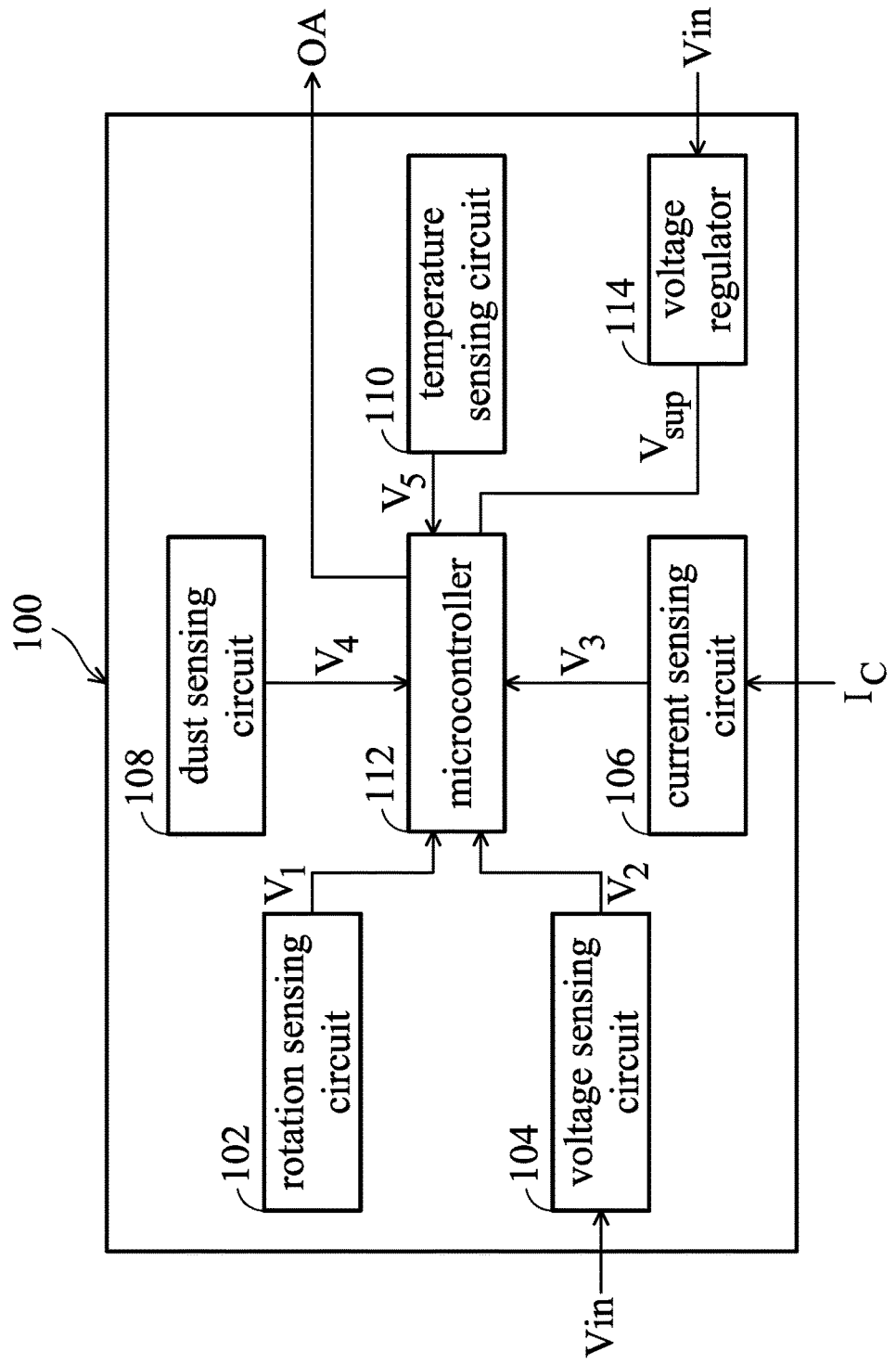
FIG. 1 is a block diagram of an monitor circuit according to an embodiment of the invention.

Please refer to FIG. 1, which is a block diagram of a monitor circuit 100 according to an embodiment of the present invention. The monitor circuit 100 is applied to a fan (not shown in the figure) and receives a driving current Ic and a driving voltage Vin, and the monitor circuit 100 can monitor various statuses (such as voltage, current and temperature) of the fan. The monitor circuit 100 can be integrated in a driving circuit board of the fan, but not limited thereto. For example, the monitor circuit 100 can be separated from the driving circuit board and connected to the driving circuit board of the fan by a connector. The monitor circuit 100 includes a plurality of sensing circuits, and the sensing circuits are used for respectively sensing a plurality of corresponding statuses of the fan, so as to obtain a plurality of corresponding sensing values. In this embodiment, the monitor circuit 100 can include a rotation sensing circuit 102, a voltage sensing circuit 104, a current sensing circuit 106, a dust sensing circuit 108, a temperature sensing circuit 110 and a microcontroller 112. Furthermore, the monitor circuit 100 can further include a voltage regulator 114 for transforming the driving voltage Vin to a supply voltage Vsup for powering the monitor circuit 100. For example, the supply voltage Vsup can be provided to the rotation sensing circuit 102, the current sensing circuit 106, the dust sensing circuit 108, the temperature sensing circuit 110 and the microcontroller 112 with electricity.

The rotation sensing circuit 102 senses a rotating status of the fan to obtain a sensing value V1 to be transferred to the microcontroller 112. The voltage sensing circuit 104 receives the driving voltage Vin and outputs a second sensing value V2 to the microcontroller 112, and the second sensing value V2 is proportional to the driving voltage Vin. The current sensing circuit 106 receives the driving current Ic and outputs a third sensing value V3 to the microcontroller 112, and the third sensing value V3 is proportional to or inversely proportional to the driving current Ic. The dust sensing circuit 108 senses dust accumulated in the fan and outputs a fourth sensing value V4 to the microcontroller 112. The temperature sensing circuit 110 senses the temperature of the fan and outputs a fifth sensing value V5 to the microcontroller 112, and the fifth sensing value V5 is proportional to or inversely proportional to the temperature. The sensing value V1, the second sensing value V2, the third sensing value V3, the fourth sensing value V4, and the fifth sensing value V5 are voltage values.

Figure 2:
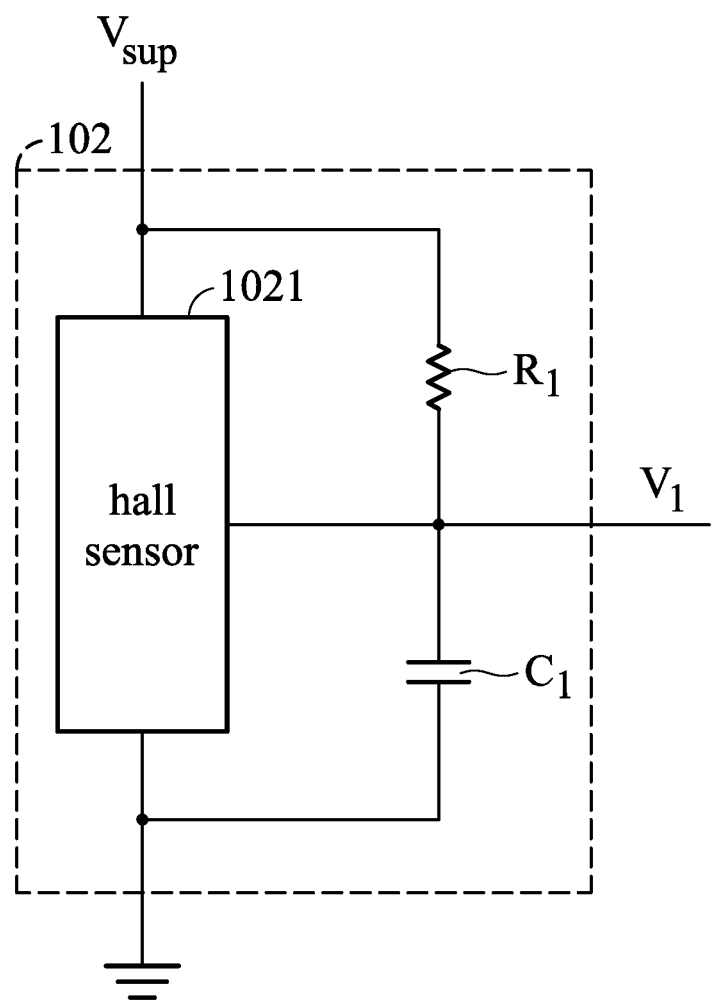
FIG. 2 is a diagram of a rotation sensing circuit according to an embodiment of the invention.

Please refer to FIG. 2, which is a diagram of the rotation sensing circuit 102 according to an embodiment of the present invention. The rotation sensing circuit 102 includes a Hall sensor 1021, a resistor R1, and a capacitor C1. The resistor R1 includes a first end and a second end, and the first end of the resistor R1 is connected to the supply voltage Vsup. The capacitor C1 includes a first end and a second end. The first end of the capacitor C1 is connected to the second end of the resistor R1, and the second end of the capacitor C1 is connected to a ground terminal. A first end of the Hall sensor 1021 is connected to the supply voltage Vsup, and a second end of the Hall sensor 1021 is connected to the ground terminal. The Hall sensor 1021 can output a Hall voltage to serve as the sensing value V1 according to a rotating status of the fan. For example, when the fan rotates for one circle, the Hall sensor 1021 outputs the sensing value V1 in the form of a pulse or a square wave. Therefore, when the fan continues rotating, the sensing value V1 is a waveform in the form of continuous pulses or continuous square waves. In addition, the microcontroller 112 has a function for counting, i.e., served as a counter, and the microcontroller 112 can calculate a total number of rotations of the fan according to the sensing values V1, and the total number of rotations serves as a first sensing value.

Figure 3:
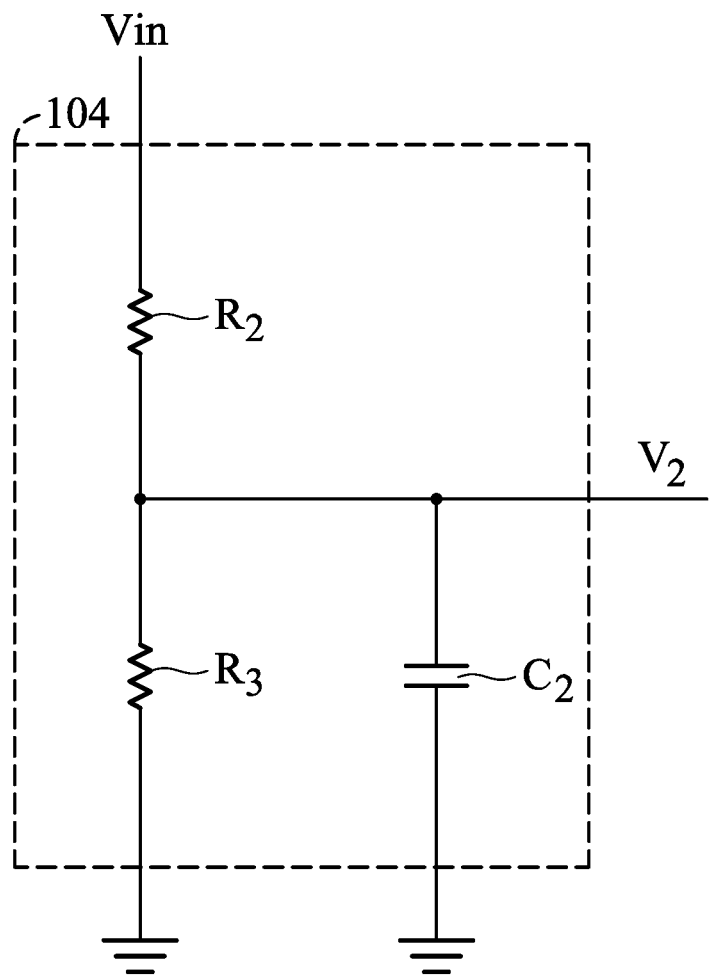
FIG. 3 is a diagram of voltage sensing circuit according to an embodiment of the invention.

Please refer to FIG. 3, which is a diagram of the voltage sensing circuit 104 according to an embodiment of the present invention. The voltage sensing circuit 104 includes a resistor R2, a resistor R3, and a capacitor C2. The resistor R2 includes a first end and a second end, and the first end of the resistor R2 is connected to the driving voltage Vin. The resistor R3 includes a first end and a second end. The first end of the resistor R3 is connected to the second end of the resistor R2, and the second end of the resistor R3 is connected to the ground terminal. The capacitor C2 includes a first end and a second end. The first end of the capacitor C2 is connected to the first end of the resistor R3 and the microcontroller 112, and the second end of the capacitor C2 is connected to the around terminal. The voltage sensing circuit 104 receives the driving voltage Vin and then providing the second sensing value V2 to the microcontroller 112 through the first end of the capacitor C2. The second sensing value V2 is proportional to the driving voltage Vin.

Figure 4:
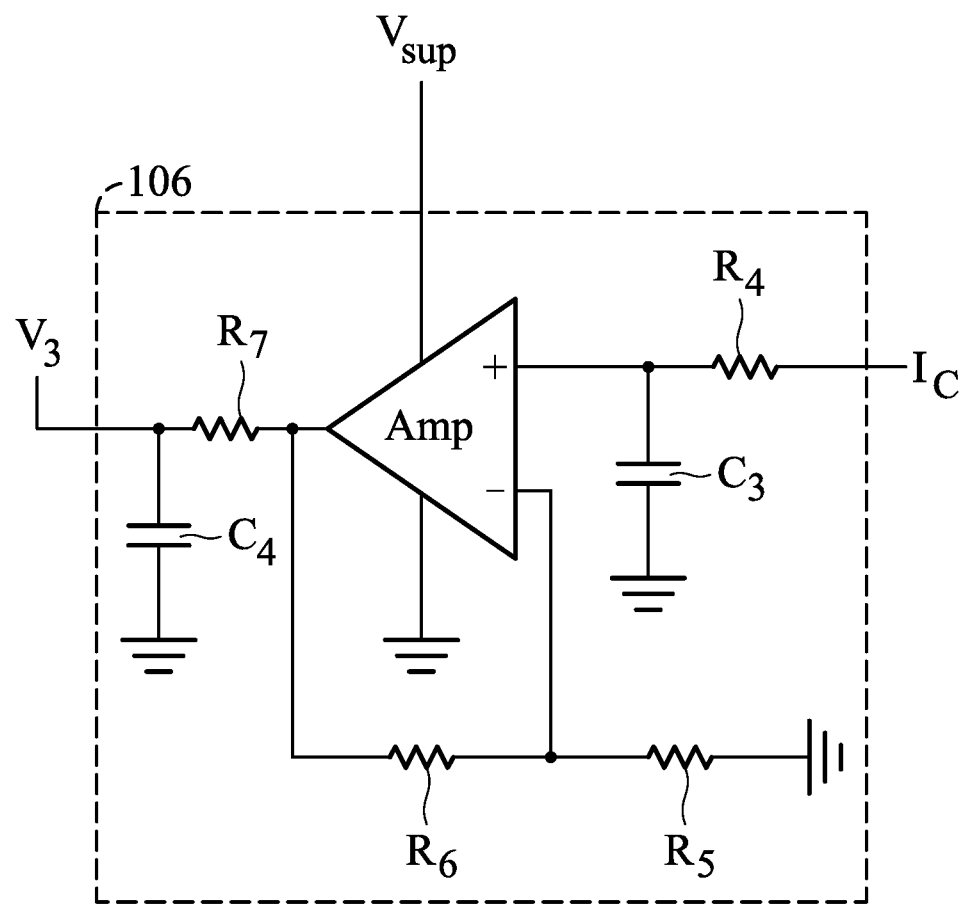
FIG. 4 is a diagram of a current sensing circuit according to an embodiment of the invention.

Please refer to FIG. 4, which is a diagram of the current sensing circuit 106 according to an embodiment of the present invention. The current sensing circuit 106 includes an operational amplifier Amp, a resistor R4, a resistor R5, a resistor R6, a resistor R7, a capacitor C3, and a capacitor C4. The operational amplifier Amp includes a first end and a second end. The first end of the operational amplifier Amp is connected to the supply voltage Vsup, and the second end of the operational amplifier Amp is connected to a ground terminal. The resistor R4 includes a first end and a second end. The first end of the resistor R4 is connected to the driving current Ic, and the second end of the resistor R4 is connected to a non-inverting input terminal of the operational amplifier Amp. The capacitor C3 includes a first end and a second end. The first end of the capacitor C3 is connected to the second end of the resistor R4, and the second end of the capacitor C3 is connected to the ground terminal.

The resistor R5 includes a first end and a second end. The first end of the resistor R5 is connected to an inverting input terminal of the operational amplifier Amp, and the second end of the resistor R5 is connected to the ground terminal. The resistor R6 includes a first end and a second end. The first end of the resistor R6 is connected to an output terminal of the operational amplifier Amp, and the second end of the resistor R6 is connected to the first end of the resistor R5. The resistor R7 includes a first end and a second end. The first end of the resistor R7 is connected to the output terminal of the operational amplifier Amp, and the second end of the resistor R7 is connected to the microcontroller 112, so as to provide the third sensing value V3. The capacitor C4 includes a first end and a second end. The first end of the capacitor C4 is connected to the second end of the resistor R7, and the second end of the capacitor C4 is connected to the ground terminal. The current sensing circuit 106 receives the driving current Ic and then providing the third sensing value V3 to the microcontroller 112. The third sensing value V3 is proportional to or inversely proportional to the driving current Ic.

Figure 5:
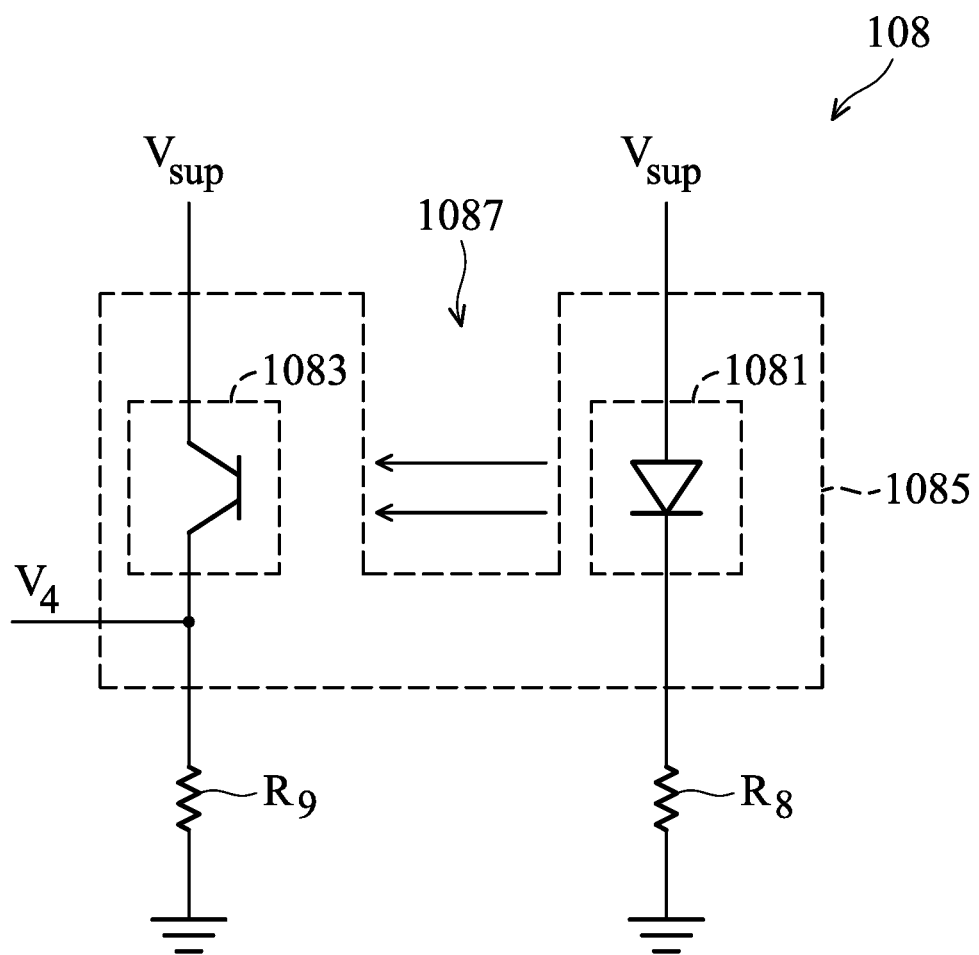
FIG. 5 is a diagram of a dust sensing circuit according to an embodiment of the invention.

Please refer to FIG. 5, which is a diagram of the dust sensing circuit 108 according to an embodiment of the present invention. The dust sensing circuit 108 senses dust accumulated in the fan and then outputs a fourth sensing value V4 to the microcontroller 112. The dust sensing circuit 108 includes a light emitter 1081 and a light receiver 1083. In this embodiment, the light emitter 1081 can be a light emitting diode (LED), and the light receiver 1083 can be a phototransistor, but they are not limited thereto. For example, the light receiver 1083 can also be a photo diode. Generally speaking, the light emitter 1081 and the light receiver 1083 are installed inside a casing 1085, and the casing 1085 includes a notch 1087 as shown in the figure. The light emitter 1081 includes a first end and a second end. The first end of the light emitter 1081 is connected to the supply voltage Vsup, and the second end of the light emitter 1081 is connected to a first end of a resistor R8. A second end of the resistor R8 is connected to the ground terminal. The light receiver 1083 includes a first end and a second end. The first end of the light receiver 1083 is connected to the supply voltage Vsup, and the second end of the light receiver 1083 is connected to a first end of a resistor R9. A second end of the resistor R9 is connected to the ground terminal. The light emitter 1081 emits a plurality of light beams, the light receiver 1083 receives the light beams emitted by the light emitter 1081, and then the light receiver 1083 provides the fourth sensing value V4 to the microcontroller 112 through the second end of the light receiver 1083. In this embodiment, when dust accumulates in the notch 1087 and the light receiver 1083 cannot receive the light beams from the light emitter 1081, the fourth sensing value V4 can be changed or adjusted from a low-voltage level to a high-voltage level, such as changing from resistor 0.3 volts to 0.5 volts, but it is not limited thereto.

Figure 6:
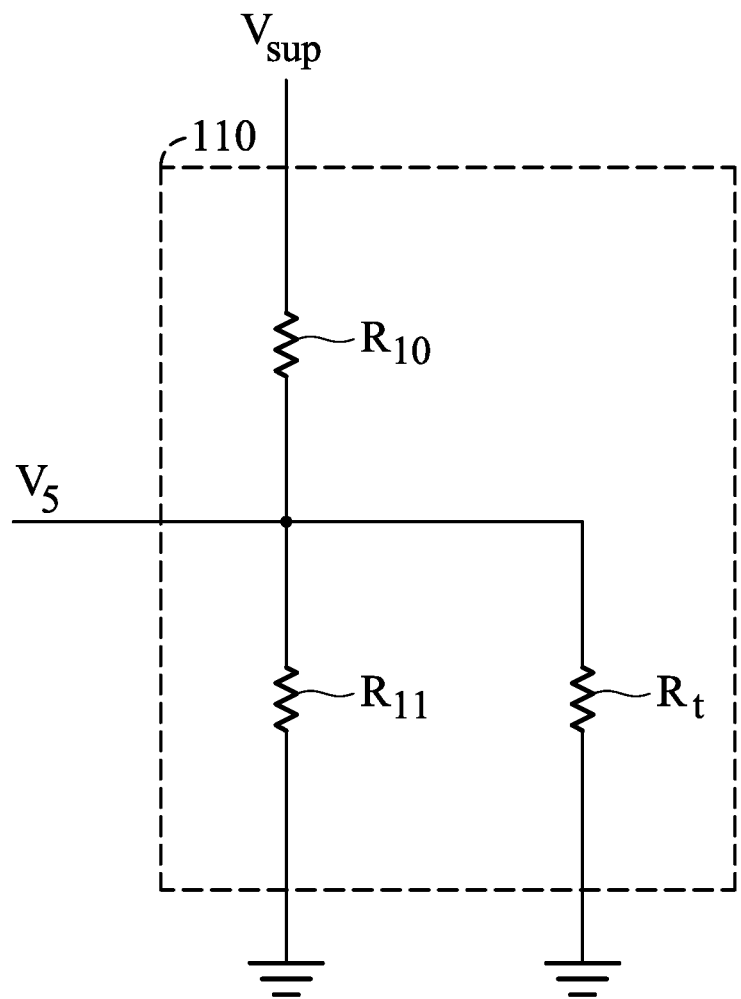
FIG. 6 is a diagram of a temperature sensing circuit according to an embodiment of the invention.

Please refer to FIG. 6, which is a diagram of the temperature sensing circuit 110 according to an embodiment of the present invention. The temperature sensing circuit 110 senses the temperature of the fan and then outputs the fifth sensing value V5 to the microcontroller 112. The fifth sensing value V5 is proportional to or inversely proportional to the temperature. The temperature sensing circuit 110 includes a resistor R10, a resistor R11, and a thermistor Rt. The resistor R10 includes a first end and a second end. The first end of the resistor R10 is connected to the supply voltage Vsup. The resistor R11 includes a first end and a second end. The first end of the resistor R11 is connected to the second end of the resistor R10, and the second end of the resistor R11 is connected to the ground terminal. The thermistor Rt includes a first end and a second end. The first end of the thermistor Rt is connected to the first end of the resistor R11 and the microcontroller 112, and the second end of the thermistor Rt is connected to the ground terminal. Because a resistor value of the thermistor Rt varies according to the temperature of the fan, the fifth sensing value V5 (i.e., the voltage value) varies along with the changing of the temperature.

A plurality of preset value ranges are stored in the microcontroller 112, and the preset value ranges include a first preset value range, a second preset value range, a third preset value range, a fourth preset value range and a fifth preset value range. The first preset value range can be a preset number of rotations which represents an upper limit of the number of rotations of the fan. If the first sensing value exceeds the preset number of rotations, it indicates that the fan may be broken. The second preset value range is a range of voltage values, such as a range from 36 volts to 70 volts. When the second sensing value V2 exceeds the range of preset voltage value, it indicates that the driving voltage Vin corresponding to the second sensing value V2 is not within a range of normal operation voltage. The third preset value range is a range of voltage values. When the third sensing value V3 exceeds the range of preset voltage value, it indicates that the driving current Ic corresponding to the third sensing value V3 is not within a range of preset normal operation current. For example, the driving current Ic is smaller than 0.2 ampere or greater than 1 ampere. The fourth preset value range is a range of voltage value, such as a range from 0 volt to 1 volts. When the dust of the fan accumulates or deposits in the notch 1087 and the light receiver 1083 cannot receive the light beams, the light receiver 1083 provides the fourth sensing value V4 (such as 1.5 volt) to the microcontroller 112. At this time, the fourth sensing value V4 exceeds the fourth preset value range, and it indicates that there is too much dust accumulated in the fan and the dust needs to be cleaned. The fifth preset value range is a range of voltage value. When the fifth sensing value V5 exceeds the range of preset voltage value, it indicates that the temperature of the fan corresponding to the fifth sensing value V5 is too high.

The microcontroller 112 can respectively check whether the first sensing value exceeds the first preset value range, whether the second sensing value V2 exceeds the second preset value range, whether the third sensing value V3 exceeds the third preset value range, whether the fourth sensing value V4 exceeds the fourth preset value range and whether the fifth sensing value V5 exceeds the fifth preset value range, so as to obtain a plurality of comparison results. Then, the microcontroller 112 outputs one of a plurality of warning signals OA according to the comparison results. Each of the warning signals OA has a specific frequency, and each of the specific frequencies is different from that of the other.

Please refer to FIG. 7, which is a diagram of a comparison table stored in a microcontroller 112 according to an embodiment of the present invention. The value of S1 is 1, indicating that the first sensing value exceeds the first preset value range, while the value of S1 is 0, indicating that the first sensing value does not exceed the first preset value range. The value of S2 is 1, indicating that the second sensing value V2 exceeds the second preset value range, while the value of S2 is 0, indicating that the second sensing value V2 does not exceed the second preset value range. The value of S3 is 1, indicating that the third sensing value V3 exceeds the third preset value range, while the value of S3 is 0, indicating that the third sensing value V3 does not exceed the third preset value range. The value of S4 is 1, indicating that the fourth sensing value V4 exceeds the fourth preset value range, while the value of S4 is 0, indicating that the fourth sensing value V4 does not exceed the fourth preset value range. The value of S5 is 1, indicating that the fifth sensing value V5 exceeds the fifth preset value range, while the value of S5 is 0, indicating that the fifth sensing value V5 does not exceed the fifth preset value range. The microcontroller 112 can check the comparison results with the comparison table so as to output one of the warning signals OA. For example, if only the second sensing value V2 exceeds the second preset value range, the microcontroller 112 determines that the comparison results conformed to condition 2 in FIG. 7 according to the comparison results and the comparison table. Therefore, the microcontroller 112 outputs a warning signal OA with a specific frequency of 20 Hz. After that, a display device, not shown in the figures, can display a warning message after receiving the warning signal OA. The warning message indicates that the driving voltage Vin is not within the range of normal operation voltage, so as to inform the user that the fan has a problem. In addition, when all the sensing values do not exceed the corresponding preset value ranges, the microcontroller 112 determines that the comparison results do not conform or index to any conditions in FIG. 7 according to the comparison result. Then, the microcontroller 112 correspondingly outputs a normal signal with a normal frequency, and the normal frequency is different from each specific frequency of the warning signals OA, such as 300 Hz. The normal signal indicates that there is no problem with the fan. It can be understood that the specific frequencies and the normal frequency are not limited to this embodiment. Specific frequencies different from each other and a normal frequency that is different from the specific frequencies are within the scope of the present invention.

Figure 8:
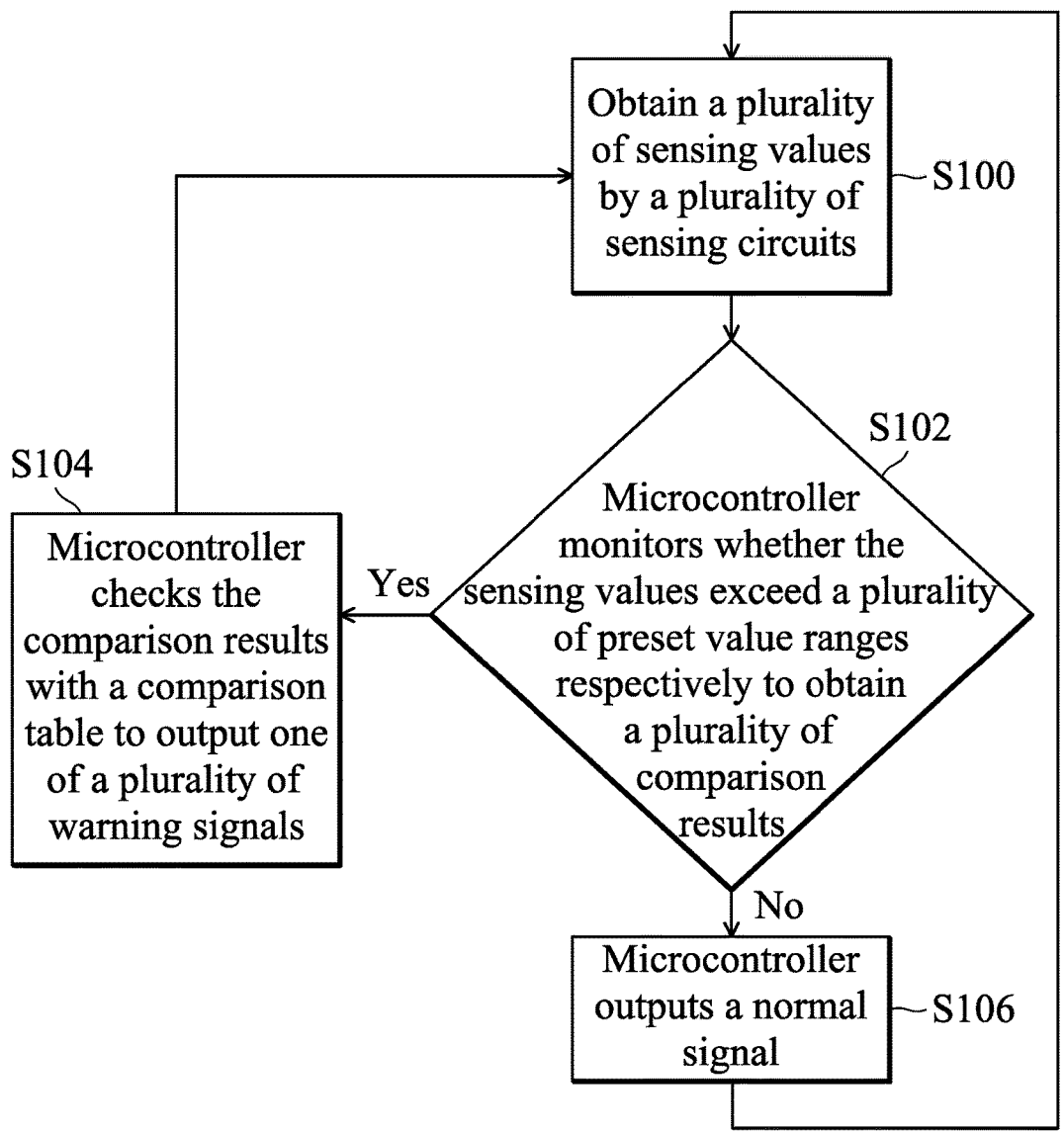
FIG. 8 is a flow chart of a monitoring method for a fan according to an embodiment of the invention.

Please refer to FIG. 8, which is a flow chart of a monitoring method for a fan according to an embodiment of the present invention. In step S100, a plurality of statuses of a fan is sensed by a plurality of sensing circuits respectively to obtain a plurality of sensing values. In step S102, the microcontroller 112 monitors whether the sensing values exceed a plurality of preset value ranges respectively to obtain a plurality of comparison results. If at least one of the sensing values exceeds the respective preset value range, step S104 is performed. If all of the sensing values do not exceed the preset value ranges respectively, step S106 is performed. In step S104, the microcontroller 112 checks the comparison results with a comparison table to output one of a plurality of warning signals OA. Each of the warning signals has a specific frequency, and the specific frequency is different from other specific frequencies. After step 104 is performed, the flow returns to step S100. In step S106, when the sensing values do not exceed the preset value ranges, the microcontroller 112 outputs a normal signal according to the comparison results, and the normal signal includes a normal frequency that is different from the specific frequencies of the warning signals OA. After step 106 is performed, the flow returns to step S100.

The invention provides a monitor circuit for monitoring various statuses of a fan. The monitor circuit can monitor whether a total number of rotations of the fan exceeds a preset rotation number, monitor whether the driving voltage and the driving current are within the respective ranges of a preset voltage and a preset current, and monitor whether the temperature of the fan exceeds a preset temperature. Therefore, the invention can solve the problems in the prior art wherein conventional fans can only detect fan problems but cannot provide further detailed information about the fan to generate a specific warning signal.

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A monitor circuit, used for a fan and receiving a driving current and a driving voltage of the fan, the monitor circuit comprising:
   a plurality of sensing circuits, the sensing circuits being respectively for sensing a plurality of statuses of the fan and obtaining a plurality of sensing values; and
   a microcontroller, for monitoring whether the sensing values exceed a plurality of preset value ranges respectively to obtain a plurality of comparison results, and the microcontroller outputting one of a plurality of warning signals according to the comparison results;
   wherein each of the warning signals has a specific frequency different from the other warning signals, wherein each of the warning signals corresponds to one condition of the fan;
   wherein when the sensing values do not exceed the preset value ranges, the microcontroller outputs a normal signal according to the comparison results, and the normal signal comprises a normal frequency that is different from the specific frequencies of the warning signals.

2. The monitor circuit as claimed in claim 1, wherein the microcontroller comprises a comparison table, and the microcontroller checks the comparison results with the comparison table to output one of the warning signals.

3. The monitor circuit as claimed in claim 1, wherein the preset value ranges comprise a first preset value range and a second preset value range, and the sensing circuits comprise:
   a rotation sensing circuit, for sensing a rotating status of the fan to obtain a first sensing value; and
   a voltage sensing circuit, for receiving the driving voltage and outputting a second sensing value;
   wherein the microcontroller monitors whether the first sensing value exceeds the first preset value range and whether the second sensing value exceeds the second preset value range, so as to obtain the comparison results, and the microcontroller outputs one of the warning signals according to the comparison results.

4. The monitor circuit as claimed in claim 3, wherein the preset value ranges further comprise a third preset value range, and the sensing circuits further comprise a current sensing circuit for receiving the driving current and outputting a third sensing value;
   wherein the microcontroller further monitors whether the third sensing value exceeds the third preset value range to obtain the comparison results, and the microcontroller outputs one of the warning signals according to the comparison results.

5. The monitor circuit as claimed in claim 4, wherein the preset value ranges further comprise a fourth preset value range, and the sensing circuits further comprise a dust sensing circuit for sensing dust accumulation and outputting a fourth sensing value;
   wherein the microcontroller further monitors whether the fourth sensing value exceed the fourth preset value range to obtain the comparison results, and the microcontroller outputs one of the warning signals according to the comparison results.

6. The monitor circuit as claimed in claim 5, wherein the preset value ranges further comprise a fifth preset value range, and the sensing circuits further comprise a temperature sensing circuit for sensing temperature of the fan and outputting a fifth sensing value;
   wherein the microcontroller further monitors whether the fifth sensing value exceeds the fifth preset value range to obtain the comparison results, and the microcontroller outputs one of the warning signals according to the comparison results.

7. The monitor circuit as claimed in claim 6, wherein the temperature sensing circuit comprises:
   a first resistor, a first end of the first resistor being connected to a supply voltage;
   a second resistor, a first end of the second resistor being connected to a second end of the first resistor, and a second end of the second resistor being connected to a ground terminal; and
   a thermistor, a first end of the thermistor being connected to the first end of the second resistor and the microcontroller, and a second end of the thermistor being connected to the ground terminal.

8. The monitor circuit as claimed in claim 4, wherein the current sensing circuit comprises:
   an operational amplifier, a first end of the operational amplifier being connected to a supply voltage, and a second end of the operational amplifier being connected to a ground terminal;
   a first resistor, a first end of the first resistor being connected to the driving current, and a second end of the first resistor being connected to a non-inverting input terminal of the operational amplifier;
   a first capacitor, a first end of the first capacitor being connected to the second end of the first resistor, and a second end of the first capacitor being connected to the ground terminal;
   a second resistor, a first end of the second resistor being connected to an inverting input terminal of the operational amplifier, and a second end of the second resistor being connected to the ground terminal;
   a third resistor, a first end of the third resistor being connected to an output terminal of the operational amplifier, and a second end of the third resistor being connected to the first end of the second resistor;
   a fourth resistor, a first end of the fourth resistor being connected to the output terminal of the operational amplifier, and a second end of the fourth resistor being connected to the microcontroller; and a second capacitor, a first end of the second capacitor being connected to the second end of the fourth resistor, and a second end of the second capacitor being connected to the ground terminal.

9. The monitor circuit as claimed in claim 5, wherein the dust sensing circuit comprises:
   a light emitter, for emitting light beams; and
   a light receiver, for receiving the light beams emitted by the light emitter;
   wherein when the light receiver cannot receive the light beams, the light receiver provides the fourth sensing value to the microcontroller.

10. The monitor circuit as claimed in claim 3, wherein the rotation sensing circuit comprises:
    a Hall sensor;
    a resistor, a first end of the resistor being connected to a supply voltage; and
    a capacitor, a first end of the capacitor being connected to a second end of the resistor, and a second end of the capacitor being connected to a ground terminal;
    wherein the Hall sensor outputs a Hall voltage, the microcontroller obtains a total number of rotations of the fan according to the Hall voltage, and the total number of rotations serves as the first sensing value.

11. The monitor circuit as claimed in claim 3, wherein the voltage sensing circuit comprises:
    a first resistor, a first end of the first resistor being connected to the driving voltage;
    a second resistor, a first end of the second resistor being connected to a second end of the first resistor, and a second end of the second resistor being connected to a ground terminal; and
    a capacitor, a first end of the capacitor being connected to the first end of the second resistor, and a second end of the capacitor being connected to the ground terminal.

12. The monitor circuit as claimed in claim 1, wherein the sensing circuits comprise a rotation sensing circuit for sensing a rotating status of the fan to obtain a sensing value.

13. The monitor circuit as claimed in claim 1, wherein the sensing circuits comprise a voltage sensing circuit for receiving the driving voltage and outputting one of the sensing values, which is proportional to the driving voltage.

14. The monitor circuit as claimed in claim 1, wherein the sensing circuits comprise a current sensing circuit for receiving the driving current and outputting one of the sensing values, which is proportional to or inversely proportional to the driving current.

15. The monitor circuit as claimed in claim 1, wherein the sensing circuits comprise a dust sensing circuit for sensing dust accumulation and outputting one of the sensing values.

16. The monitor circuit as claimed in claim 15, wherein the dust sensing circuit comprises:
    a light emitter, for emitting a plurality of light beams; and
    a light receiver, for receiving the light beams emitted by the light emitter;
    wherein when the light receiver cannot receive the light beams, the light receiver provides one of the sensing values to the microcontroller.

17. The monitor circuit as claimed in claim 1, wherein the sensing circuits comprise a temperature sensing circuit for sensing temperature of the fan and outputting one of the sensing values, and the one of the sensing values is proportional to or inversely proportional to the temperature.

18. The monitor circuit as claimed in claim 1, further comprising a voltage regulator for transforming the driving voltage to a supply voltage for powering.

19. A monitoring method, comprising:
    sensing a plurality of statuses of a fan by a plurality of sensing circuits respectively to obtain a plurality of sensing values;
    monitoring whether the sensing values exceed a plurality of preset value ranges respectively to obtain a plurality of comparison results; and
    outputting one of a plurality of warning signals by the microcontroller according to the comparison results;
    wherein each of the warning signals comprises a specific frequency different from the other warning signals, wherein each of the warning signals corresponds to one condition of the fan;
    wherein when the sensing values do not exceed the corresponding preset value ranges, the microcontroller outputs a normal signal according to the comparison results, and the normal signal comprises a normal frequency that is different from the specific frequencies of the warning signals.

20. The monitoring method as claimed in claim 19, wherein the step of outputting one of a plurality of warning signals by the microcontroller according to the comparison results comprises:
    the microcontroller checks the comparison results with a comparison table to output one of the warning signals.

* * * * *